United States Patent [19]
Wong

[11] Patent Number: 5,833,461
[45] Date of Patent: *Nov. 10, 1998

[54] ADHERING PREFORMED POSTERIOR PALATAL SEAL FORMING DENTURES AND METHOD

[76] Inventor: Nelson J. Wong, 2101 Midway Rd., Ste. 250, Carrollton, Tex. 75006

[ * ] Notice: The term of this patent shall not extend beyond the expiration date of Pat. No. 5,490,782.

[21] Appl. No.: 542,510

[22] Filed: Oct. 11, 1995

Related U.S. Application Data

[62] Division of Ser. No. 280,062, Jul. 25, 1994, Pat. No. 5,718,584, and a division of Ser. No. 182,810, Jan. 14, 1994, Pat. No. 5,490,782.

[51] Int. Cl.⁶ .................................................. A61C 13/02
[52] U.S. Cl. ..................................... 433/168.1; 433/199.1
[58] Field of Search ................................ 433/167, 168.1, 433/171, 199.1, 213, 184, 188

[56] References Cited

U.S. PATENT DOCUMENTS

| | | |
|---|---|---|
| 514,201 | 2/1894 | Robertson . |
| 729,621 | 3/1903 | Malone . |
| 1,729,461 | 9/1929 | Thayer . |
| 2,101,431 | 12/1937 | Groff . |
| 2,171,736 | 9/1939 | Ballard ........................................ 18/55.1 |
| 2,663,933 | 12/1953 | Avery .................................... 433/168.1 |
| 2,768,440 | 10/1956 | Elliott . |
| 2,985,961 | 5/1961 | Schwartz . |
| 3,335,495 | 8/1967 | Wichner . |
| 3,464,111 | 9/1969 | Gillard . |
| 3,567,806 | 3/1971 | Dyal ........................................... 264/18 |
| 3,621,575 | 11/1971 | Schneider et al. . |
| 3,644,996 | 2/1972 | Weinkle . |
| 3,667,123 | 6/1972 | Huey . |
| 3,783,514 | 1/1974 | Kersten . |
| 3,839,796 | 10/1974 | Hazar . |
| 3,846,911 | 11/1974 | Wichner . |
| 4,017,971 | 4/1977 | Hazar . |
| 4,019,253 | 4/1977 | Hazar . |
| 4,097,992 | 7/1978 | Hazar . |
| 4,161,065 | 7/1979 | Gigante . |
| 4,247,287 | 1/1981 | Gigante ................................... 433/199 |
| 4,337,042 | 6/1982 | von Nostitz ............................ 433/171 |
| 4,370,133 | 1/1983 | Stempel ................................. 433/171 |
| 4,470,815 | 9/1984 | Hazar ..................................... 433/171 |
| 4,583,947 | 4/1986 | Hazar ..................................... 433/171 |
| 4,932,869 | 6/1990 | Bergeron ................................ 433/167 |

OTHER PUBLICATIONS

Richard W. Brand and Donald E. Isselhard, Oral Cavity Proper, *Anatomy of Orofacial Structures*, (St. Louis: The C. V. Mosby Company, 1977), pp. 333–335.

J. A. Hobkirk, "Decisions to be Made Before the Next Visit," *Complete Dentures*, (Surrey: Adlard & Son 1986), pp. 78–81.

Gino Passamonti, "Posterior Limit and Posterior Seal," *Atlas of Complete Dentures*, (Berlin: Quintessence Publishing Co., Inc., 1979), pp. 90–97.

David M. Watt and A. Roy MacGregor, "Retention," *Designing Complete Dentures* (Surrey: Adlard & Son 1986), pp. 54–57, 198.

Marc Appelbaum, "The Posterior Palatal Seal," *Essentials of Complete Denture Prosthodontics*, (Philadelphia: W. B. Saunders Company 1979), pp. 171–192.

(List continued on next page.)

*Primary Examiner*—Cary E. O'Connor
*Attorney, Agent, or Firm*—Gardere & Wynne, LLP; John W. Montgomery

[57] ABSTRACT

A preformed posterior palatal seal (Preformed PPS) for use in preparation of dentures includes a body preformed of a predetermined Anatomically based size and shape of a posterior palatal seal (PPS) for sealing a denture at the "Ah line" of the human palate and adhesive for holding the preformed body to a denture impression prior to forming a mold from which a denture is to be formed.

3 Claims, 3 Drawing Sheets

OTHER PUBLICATIONS

John D. Jones, "A Qualitative Comparison of Various Record Base Materials," *The Journal of Prosthetic Dentistry*, 49, No. 1, Jan. 1983 –pp. 130–132.

Joseph Nassif and Russell Jumbelic, "Dupicating Maxillary Complete Dentures," *The Journal of Prosthetic Dentistry*, 52, No. 5 Nov. 1984, pp. 753–755.

Hyman Kotkin, "Diagnostic Significance of Denture Complaints," *The Journal of Prosthetic Dentistry*, 53, No. 1, Jan. 1985, pp. 73–77.

Joe H. Jaggers, Nikzad S. Javid and Frank A. Colaizzi, "Complete Denture Curriculum Survey of Dental Schools in the United States," *The Journal of Prosthetic Dentistry*, 53, No. 5, May 1985 pp. 736–739.

Bernard Levin and John L. Sanders, "Results of a Survey of Complete Denture Procedures Taught in American and Canadian Dental Schools: An Update," *The Journal of Prosthetic Dentistry*, 54, No. 2, Aug. 1985, pp. 302–306.

Arthur Nimmo, "Correction of the Posterior Palatal Seal By Using a Visible Light–Cured Resin: A Clinical Report," *The Journal of Prosthetic Dentistry*, 59, No. 5, May 1988, pp. 529–531.

W. P. Naylor and J. D. Rempala, "The Posterior Palatal Seal—Its Forms and Functions (II)—Design and Cast Preparation," *QDT* (Quintessence of Dental Technology), 10, No. 8, Sep. 1986, pp. 489–492.

W. Patrick Naylor and Vincent A. Stephens, "Location and Transfer of the Vibrating Line: Clinical and Laboratory Techniques," *QDT* (Quintessence of Dental Technology), 10, No. 9, Oct. 1986, pp. 557–559.

J. A. von Fraunhofer, Z. Khan and R. Razavi, "The Effect of the Posterior Palatal Seal on the Strength of Maxillary Denture Bases," *QDT* (Quintessence of Dental Technology), 11, No. 3, Jun. 1987, pp. 193–194.

Hiroshi Muraoka, "Adding a Posterior Palatal Seal," *A Color Atlas of Complete Denture Fabrication* (Tokyo: Quintessence Publishing Company, 1989), pp. 6, 409–412.

Robert M. Morrow, Kenneth D. Rudd and John E. Rhoads, "Posterior Palatal Seal," *Dental Laboratory Procedures* (St. Louis: The C. V. Mosby Company, 1986), pp. 125–128.

Judson C. Hickey, George A. Zarb and Charles L. Bolender, "Perfection of the Posterior Palatal Seal," *Prosthodontic Treatment for Edentulous Patients* (9th Ed.) (St. Louis: The C. V. Mosby Company, 1985), pp. 422–426.

Marc Appelbaum, "The Posterior Palatal Seal," *Essentials of Complete Denture Prosthodontics* (2nd Ed.) (Massachusetts: PSG Publishing Company, 1984), pp. 107–122.

Bernard Levin, "Completion of Master Casts and Carving the Posterior Palatal Seal," *Impressions for Complete Dentures* (Chicago: Quintessence Publishing Company, Inc., 1984), pp. 143, 147, 150–161, 168–170 and 180–186.

William E. Avant, "A Comparison of the Retention of Complete Denture Bases Having Different Types of Posterior Palatal Seal," *The Journal of Prosthetic Dentistry*, 29, No. 5, May 1973, pp. 484–493.

A. A. Calomeni, E. E. Feldmann and W. A. Kuebker, "Posterior Palatal Seal Location and Preparation on the Maxillary Complete Denture Cast," *The Journal of Prosthetic Dentistry*, 49, No. 5, May 1983, pp. 628–630.

Frank R. Lauciello and Salvatore P. Conti, "A Method of Correcting the Posterior Palatal Seal Area of a Maxillary Complete Denture," *The Journal of Prosthetic Dentistry* (vol. 42, No. 6) Dec. 1979 –pp. 690–692.

Ernest A. Carroll and Francis W. Shaffer, "Redefining the Posterior Palatal Seal on a Complete Denture," *The Journal of Prosthetic Dentistry*, 43, No. 1, Jan. 1980, pp. 105–107.

Gerald N. Graser, "Review of the Literature: Predoctoral Removable Prosthodontics Education," *The Journal of Prosthetic Dentistry*, 64, No. 3, Sep. 1990, pp. 326–333.

Glossary of Prosthodontic Terms, *The Journal of Prosthetic Dentistry*, 58, No. 6, Dec. 1987, p. 750.

Kenneth B. May, Michael E. Rozzoog, Andrew Koran III and Emerson Robinson, "Denture Base Resins: Comparison Study of Color Stability," *The Journal of Prosthetic Dentistry*, 68, No. 1, pp. 78–82.

Dale E. Smith, "Color Stability of Long–Term Soft Denture Liners," *The Journal of Prosthetic Dentistry*, 68, No. 5, Nov. 1992, pp. 836–838.

Zafrulla Khan and C. Brent Haeberle, "One–appointment Construction of an Immediate Transitional Complete Denture Using visible Light–Cured Resin," *The Journal of Prosthetic Dentistry*, 68, No. 3, Sep., 1992, pp. 500–502.

Dale E. Smith, "Annual Review of Selected Dental Literature: Report of the Committee on Scientific Investigation of the American Academy of Restorative Dentistry," *The Journal of Prosthetic Dentistry*, 70, No. 1, Jul. 1993, pp. 44, 78 and 85.

Jay Steinberg, "A Teaching Aid for the Visualization of the Posterior Palatal Seal Using a Modified Base Tray," *The Journal of Prosthetic Dentistry*, 67, No. 6, Jun. 1992, pp. 897–899.

G. Gauthier, J. E. Williams and J. D. Zwemer, "The Practice of Complete Denture Prosthodontics by Selected Dental Graduates," *The Journal of Prosthetic Dentistry*, 68, No. 2, Aug. 1992, pp. 308–313.

W. D. Schwarz, "The Post Dam," *Dental Update*, 18, No. 18, Jan./Feb. 1991, pp. 26–30.

"How to Bond Acrylic to Metal in Three Minutes (and why you'd want to)," advertisement for 4–META Solder starter kit (one–page).

Carol A. Lefebvre, Kent L. Knoernschild and Arthur O. Rahn, "Enhancing Retention in Complete Dentures for Patients with Atypical Muscle Attachments: Case Reports," *Quintessence International*, 24, No. 10, 1993, pp. 753–755.

Carton containing 12 EZO Upper Heavy Denture Cushions (U.S. Patent No. 2,897,593) (front and back views of carton).

JELENKO Dental Health Products Catalog: Table of Contents (pp. 2–3), Waxing section of Merchandise (pp. 36–38) and Price List (pp. 10–11) (1993).

NOBILIUM COMPANY Products Catalog: Plastic Preforms & Waxes section (pp. 11–15).

NOBILIUM COMPANY Catalog Supplement.

AUSTENAL, INC. Laboratory Products Price List, Effective Apr. 1991, p. 1; Insert to Price List, "PATTERNS".

AUSTENAL, INC. Sealon Anatomical Patterns, Upper Labio–Buccal Patterns and Lower Labio–Buccal Patterns.

ADHERING PREFORMED POSTERIOR PALATAL SEAL FORMING DENTURES AND METHOD

RELATED U.S. APPLICATIONS

This is a Divisional Application of U.S. patent application Ser. No. 08/280,062, filed Jul. 25, 1994, now U.S. Pat. No. 5,718,554, which is a continuation-in-part of U.S. patent application Ser. No. 08/182,810, filed Jan. 14, 1994, now U.S. Pat. No. 5,490,782 which are hereby incorporated by reference for all purposes as if fully set forth herein.

TECHNICAL FIELD OF THE INVENTION

The present invention relates to devices and methods that facilitate formulation of posterior palatal seals (PPS) on upper dentures and particularly, to devices and molding processes by which effective PPS may be formed.

BACKGROUND OF THE INVENTION

Millions of people throughout the world, including as many as twenty million Americans are edentulous (toothless) and rely on full dentures for function and esthetics. In fabricating dentures, it is crucial for the dentist to assure that the upper denture is well-fitted and secure. This is important not only in speech and mastication, but also in avoiding the embarrassment of a loose or falling denture.

A secure denture is usually accomplished by the denture adapting well to the gum tissue, and in the case of the upper member of dentures, through the use of a posterior palatal seal (PPS). The combination of a well-fitting denture and a well-fitting PPS will create suction or vacuum once the upper denture is seated in the mouth. A PPS is a thickened posterior portion of the upper denture border extending across the palate from the left to the right maxillary tuberosity. The increased thickness of the denture along a narrow border adds "pressure" on the tissue and maintains a vacuum seal. Without this sealing effect created by the PPS, the upper denture "leaks" (the vacuum between the denture and the roof of the mouth is reduced or lost) and the denture loosens as the wearer talks, chews or swallows.

A PPS is beneficial and considered necessary by many dentists because the border of the upper denture at the posterior palate area rests on the junction between the hard and soft palate. Unless there is additional pressure against that area of the palate, there will be loss of suction during function. Anatomically, the key effective sealing area corresponds to the junction between the hard and soft palate. Among dentists, this is also called the "Ah-Line." In locating how far a denture should extend backwards, the dentist may ask the patient to repeat the "ah" sound. In doing so, the soft palate vibrates and the hard palate does not vibrate so that the demarcation between the soft and hard palate is discernible. This is typically where the denture border will lie. The junction between the hard and soft palate where the denture border lies is neither a straight line nor of uniform consistency. It is harder in the midline and soft on both sides of the midline. A well constructed PPS, therefore, has to reflect the anatomy and features of that part of the mouth.

Presently, the most common method of fabrication of the PPS requires either a dentist or a laboratory technician to carve an indentation channel on a plaster model obtained from an impression of the toothless mouth. The impression material is typically alginate, silicon, zinc oxide-eugenol or a rubber base material. The dentist normally takes an impression of the edentulous mouth and often prepares a plaster (or dental stone) model from the impression by pouring wet plaster onto the impression. Alternatively, the impression is boxed and sent to a dental lab for preparation of a plaster or dental stone model. When the plaster has set hard, it is separated from the impression. Either a dentist or a lab technician then carves an indentation on the plaster model where the PPS will be. The depth of carvings for the PPS preferably corresponds to the anatomical qualities of the area of the palate mentioned above. That is, to be an effective seal, less must be carved away from the midline where the palate tissue is hard and more on both sides of the midline where the palate tissue is softer. The carved portion is gradually deepened as it reaches the posterior border. If all goes well, the carving results in a "Cupid's Bow" like appearance with the "string" part of the bow at the denture border and the "serpentine bow" towards the front part of the mouth. Shallowest at the "serpentine bow", it deepens going towards the "string" of the bow ( at the border of the denture ) with the deepest on both sides of the midline and shallower at the midline of this "bow" and also the two ends of this "bow." If the "carver" lacks skill or if short cuts are taken, a simple groove might be carved or a denture might be formed without a PPS of any kind.

Carving methods are taught in practically every dental school and various shapes of PPS are practiced by most denture technicians. The carving method for forming a good PPS is tedious, time-consuming and the results are inconsistent. Some technicians simply carve a trench instead of a bow shape or another approximation of a "Cupid's bow" shape either because it saves time, because they lack a high degree or skill, or because they do not understand oral anatomy and physiology. The method of hand carving a "Cupid's bow" continues to be described and recommended by professors at reputable dental schools and major international journal articles, as for example in *Quintessence, Int.*, 1993; 24:753–755.

Another less prevalent method of forming a PPS is termed a functional method or a waxing method. This method if currently more tedious and more time-consuming than the carving method. During an impression visit. the dentist applies a wax material on the impression in the poster palatal area of the impression. Again, a Cupid's bow shape provides an effective seal. A special wax is used which liquifies at mouth temperature and solidifies at room temperature. The wax is carefully shaped as by dabbing, brushing or otherwise placing it bit-by-bit and smoothing it onto the impression along the identified "Ah line." The impression is reinserted into the patient's mouth and held for several minutes to allow partial liquification and plastic deformation into and along the actual functional border between the hard and soft palate. The impression is then removed and carefully boxed to ship it to the dental lab for pouring of a plastic or a dental stone mold from which a denture will be molded. The wax must be maintained in a solidified condition during pouring so that a PPS channel will be formed in the mold. This channel in the mold will result in a raised PPS in the molded denture.

The process of forming a PPS on an existing denture has many steps and is time-consuming. The technician has to lubricate the denture; pour up a plaster model onto the denture; separate the model from the denture; carve the needed void for the PPS from the plaster model as described earlier; lubricate the model so that new denture material will not stick to the model; place new denture material into the carved void between the model and the denture; apply pressure so there is intimate contact between the new material and the denture base; wait for chemical bonding and curing of the new material; separate the denture from the model; and smooth and polish it for delivery to wearer.

SUMMARY OF THE INVENTION

The present invention uniquely provides a Preformed Posterior Palatal Seal (Preformed PPS) for use in upper dentures which can be applied onto the denture impression. Methods of applying the Preformed PPS are also provided for new denture formation. In the case of new dentures, the Preformed PPS is preferably soft, pliable and maybe even tacky. This allows the Preformed PPS to be placed on the denture impression taken from the patient's mouth. The location of placement corresponds to the denture border, generally the junction between the soft and hard palate. Immediate placement on the impression advantageously facilitates accurate "on site" location of the Preformed PPS and thus, the resulting PPS.

The shape of the Preformed PPS advantageously corresponds consistently to the quality and anatomy of the oral tissue. Preferably, the Preformed PPS is thinner toward the front of the mouth and thicker at the rear border end. It is also preferably thinner at the mid-palate as human palate tissue is thin and bony and cannot be subjected to undue pressure from too much denture thickness. Thus, the PPS can be shaped like the Cupid's bow consistently. Variations in size and proportion according to size of the roof of the mouth may be accommodated with several sizes of Preformed PPS. The vault form of the individual mouth will be naturally accommodated by the flexibility and pliability of the Preformed PPS.

The human hand used in carving a plaster mold cannot consistently equal what this inventive Preformed PPS can generate without variation. It is an object of the invention to avoid repetitive laborious work in forming a new PPS with each denture. It is another object to obtain a consistently shaped PPS to maximize sealing with every denture created. It is another object to provide a preformed PPS for use with indirect denture impressions. In a flexible form, the Preformed PPS is placed directly onto the denture impression taken from the patient's mouth. The Preformed PPS takes up the space for that part of the model which the technician would otherwise have to carve out of the plaster to create PPS, obviating the need of carvings by hand or time to sculpt a wax seal ridge and to allow it to mold itself as part of the impression, in the patient's mouth. Advantageously, a sufficient flexible preformed PPS can follow the contours of the denture impression so that a consistently uniform sealing pressure is naturally provided. Thus, even though the mouth and the resulting impression has its own contours, the seal raises proportionately in the appropriate places.

BRIEF DESCRIPTION OF THE DRAWINGS

These and other objects, features and advantages of the invention will become more evident with reference to the drawings in which like reference numerals represent like elements and in which.

DETAILED DESCRIPTION OF THE PREFERRED EMBODIMENT

Figure 1:
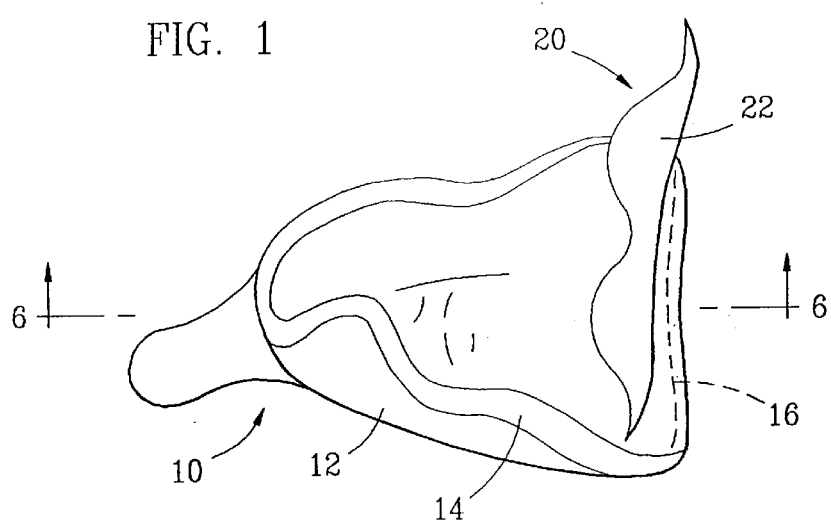
FIG. 1 is a perspective partially exploded view of an impression tray with an impression thereon for a complete denture with an embodiment of the inventive Preformed PPS shown in position for placement thereon.

FIG. 1 is a perspective view of a denture impression 10 showing one preferred embodiment of the Preformed PPS designated 20 in preparation to be placed thereon. Prior to taking this denture impression the dentist would fabricate an impression tray 12 which generally fits the contours and borders of the upper part of the edentulous mouth. Prior to taking this denture impression, the dentist would identify the "Ah-line", i.e., the junction between the hard and soft palate. The dentist asks the patient to repeat the sound "Ah", so that the vibration of the soft-palate thus initiated allows identification of the demarcation of the hard and soft palate. A marker generally of indelible ink is used to create a mark or line onto the patient's palate. While the impression is taken, the mark transfers onto the impression material 14. This is where the Preformed PPS 20 is placed so that the border of the Preformed PPS 20 coincides with the marker line 16 transferred thereon the impression material 14 on FIG. 1. Preferably, the Preformed PPS 20 has a body 22 which is in the shape of a "Cupid's bow," which shape has been found to provide a beneficial seal. Other known shapes for PPS could also be reproduced with the inventive Preformed PPS. However, the benefits of a "Cupid's bow" shaped PPS can be easily obtained by the dentist using the inventive Preformed PPS 20 without the additional carving and other steps previously required.

The denture impression 10 obtained with the "Ah-line" 16 identified as shown in FIG. 1 and with the inventive Preformed PPS 20 overlaid is thus made ready for pouring of a dental stone or a plaster, which will set in the dental impression 10. As mouth sizes vary with body size, various sizes of a Preformed PPS will be advantageous to conveniently allow construction of an effective PPS on any size denture. Preferably, three or four properly selected sizes corresponding to child, small, medium and large or other similar designations, as with standard denture molds or impression trays, could be used. The Preformed PPS 20 for this purpose should be of a pliable, flexible material, such as silicone or arginine, for example. A pliable flexible Preformed PPS will follow the contour of the impression so that it adds depth proportionately and a uniform pressure will result in the patient's mouth when a denture is formed using the Preformed PPS. As the impression is wet during handling, the Preformed PPS is preferably constructed to be able to adhere to or at least allow placement onto impression material which may be wet after removal from the patient's mouth. Thus, adhesives capable of adhesion under wet conditions may be used advantageously. In one embodiment, a separate adhesive material may be interposed between the Preformed PPS and the impression or a self-adhesive strip or tape material may be pre-formed or pre-applied directly onto the Preformed PPS. In a further preferred embodiment, the Preformed PPS may be provided with a removable non-stick sheet to prevent inadvertent sticking or it may be stored on a non-stick sheet until it is removed for application directly onto the denture impression.

Figure 2:
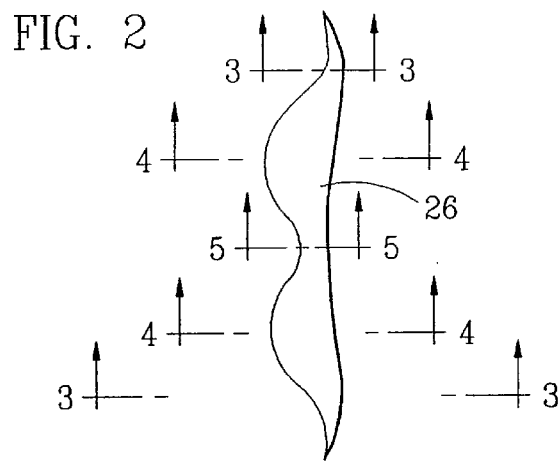
FIG. 2 is a top view of the inventive Preformed PPS as used in FIG. 1.

FIG. 2 shows a "Cupid's-bow" shaped Preformed PPS 20 from top view. A preferred shape of a Preformed PPS of this embodiment corresponds to anatomical features. The body 22 is thicker where the cross-sectional line 4—4 indicates and gradually less thick, both at mid-line, indicated by section lines 5—5 and also at the peripheral ends, represented by section lines 3—3.

Figure 3A:
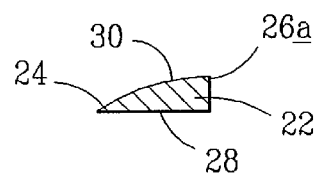
FIG. 3a is a cross-sectional view of a Preformed PPS as in FIG. 2 taken along line 3—3 showing one alternative shape.
Figure 3B:
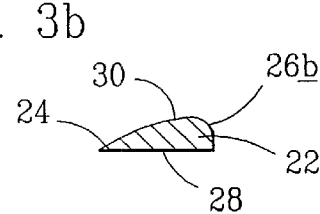
FIG. 3b is a cross-sectional view of a Preformed PPS as in FIG. 2 taken along line 3—3 showing another alternative shape.
Figure 4A:
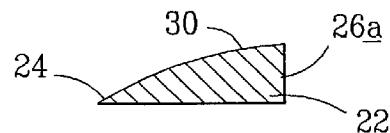
FIG. 4a is a cross-sectional view of a Preformed PPS as in FIG. 2 taken along line 4—4 showing one alternative shape.
Figure 4B:
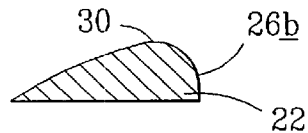
FIG. 4b is a cross-sectional view of a Preformed PPS as in FIG. 2 taken along line 4—4 showing another alternative shape.
Figure 5A:
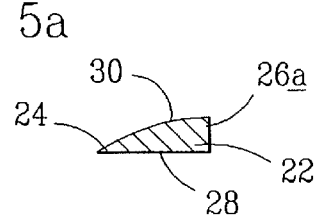
FIG. 5a is a cross-sectional view of a Preformed PPS as in FIG. 2 taken along line 5—5 showing one alternative shape.
Figure 5B:
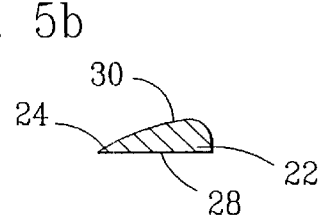
FIG. 5b is a cross-sectional view of a Preformed PPS as in FIG. 2 taken along line 5—5 showing another alternative shape.

Furthermore, the body 22 of the Preformed PPS 20 in the embodiment of FIG. 2 is tapered on side 24 towards the front (the hard-palate side of the seal). However, a rear side 26 towards the posterior denture border (the soft-palate side) is preferably formed at a right angle as shown at 26a by cross-sectional drawings in FIGS. 3a, 4a and 5a, or slightly rounded or slightly tapered according to an alternative embodiment as shown at 26b by cross-sectional drawings in FIGS. 3b, 4b and 5b. A flat base 28 of the Preformed PPS is provided for coming into contact with denture impression 14. Preferably, this base 28 will adhere to the denture impression as described above. The exposed face represented as 30, in both alternatives "a" and "b," is the face which is in contact with dental plaster or dental stone 32 when the impression is "poured" with fluid plaster or dental stone is poured into the impression 10 to form a denture model 34.

Figure 6:
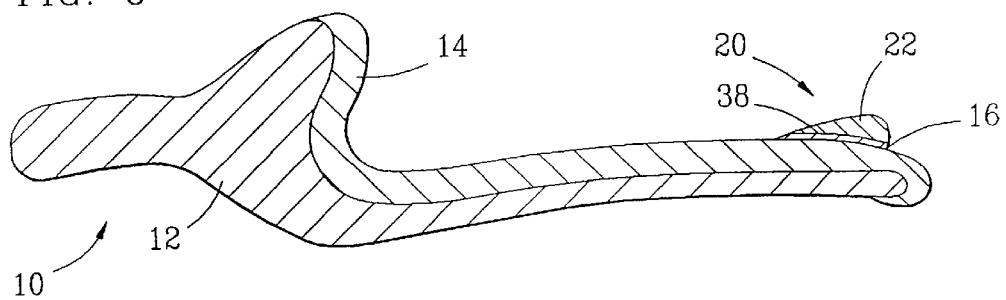
FIG. 6 is a cross-sectional view of the inventive Preformed PPS placed on an impression for complete dentures taken along section line 6—6 of FIG. 1.

FIG. 6 is a cross-sectional view of the Preformed PPS 20 placed onto the denture impression 10. The impression face 28 of the Preformed PPS. (shown in FIGS. 3, 4 and 5) goes onto the impression 10 guided by the marker or line 16 indicating the "Ah-line", i.e., the demarcation of the hard and soft palate. The tapered side 24 of the Preformed PPS is positioned toward the front of the denture (the hard-palate side) whereas the denture border side 26 is positioned so that it lies on or near the line 16.

After the Preformed PPS 20 is properly placed and dental stone 32 poured onto the impression 10 and allowed to set, the Preformed PPS 20 takes up the volume and forms a PPS channel 36 which will be occupied by a PPS when it is ultimately incorporated in a completed denture. The denture will be molded using the poured dental stone model 34 as a mold. A hardened denture with an integrally formed PPS results. The resulting raised area of the PPS on the molded denture palate is merely polished and provides increased pressure precisely along the "Ah line", allowing a suction or vacuum to be maintained when the denture is in place in the patients mouth. The additional thickness is ground and polished off from the bottom so that a smooth, upward transition results. The newly formed denture is thus provided with a permanent PPS, which is defined during molding without the difficulties associated with hand grinding of the dental stone.

Another object is to provide a device for producing equal pressure along the seal, particularly a flexible seal which follows the terrain of the mold so that a consistent amount of pressure results.

Figure 7:
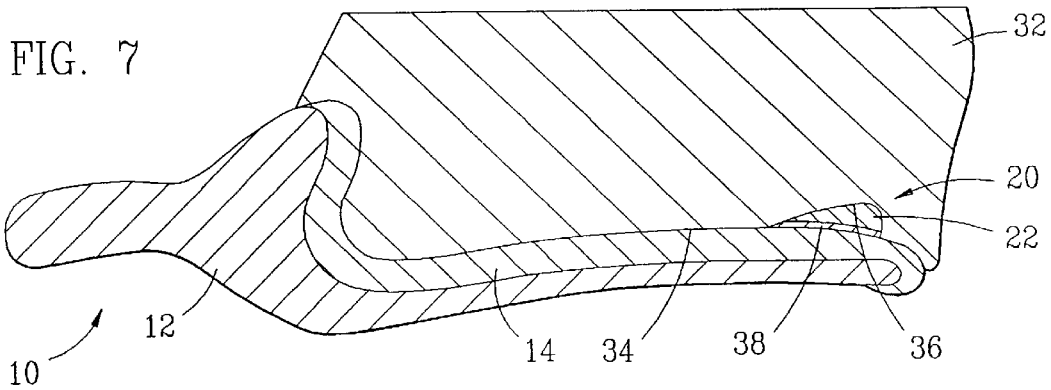
FIG. 7 is a cross-sectional view again taken along a center line of a denture impression with a dental stone poured onto the impression.

FIG. 7 is a cross-sectional view of full denture impression similar to 10 in FIG. 3 where the Preformed PPS 20 is placed properly guided by the marker line 16. The Preformed PPS 28 is adhered to the impression material with an adhesive 38. Preferably, adhesive 38 is of a type which displaces water and adheres to either zinc oxide eugenol impression material or rubber-based impression material, even when it is wet as when it is removed from the patient's mouth after the impression is taken. Here, dental stone 32 is poured and allowed to set.

Figure 8:
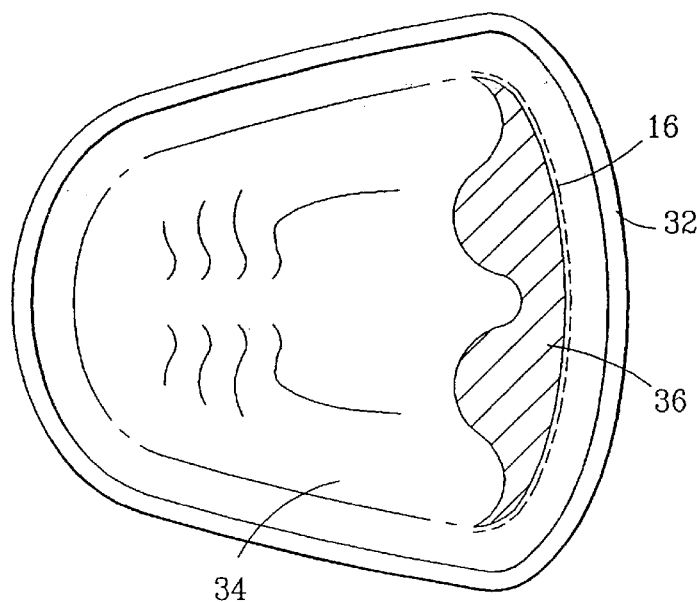
FIG. 8 is a bottom view of a dental stone model as in FIG. 7 after the stone model is separated from the impression where the inventive preformed PPS had been used.

FIG. 8 is a bottom view (i.e., corresponding to the roof of the patient's mouth) of a dental model 34 similar to the one shown being formed in FIG. 7. Once the stone model 34 is separated from the impression 10, the Preformed PPS 20 has left its impression, void or PPS channel 36 as indicated at 36. The depth and contour of the PPS impression 36 or PPS channel 36 correspond to anatomical features of the mouth as needed for a proper PPS and an effective upper denture seal.

Figure 9:
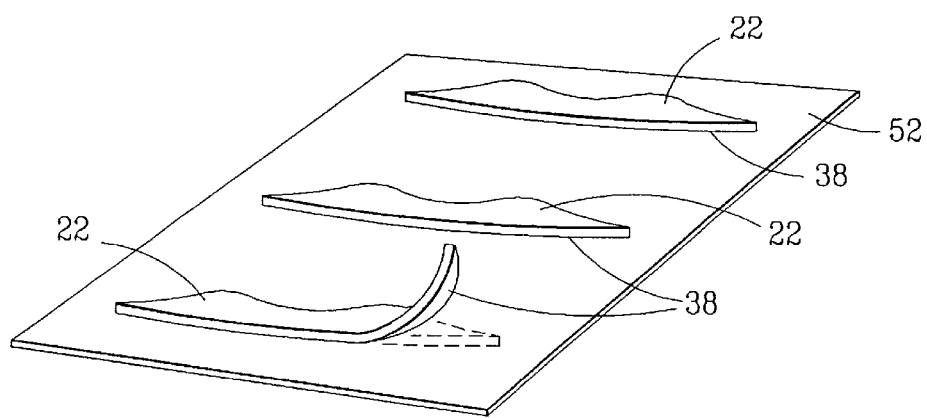
FIG. 9 is a perspective view of a self-adhesive Preformed PPS which may be applied by denture wearers to temporarily correct a malformed or an otherwise inadequate PPS until a visit to a dentist can be scheduled.

The embodiment shown in FIG. 9 provides one or more Preformed PPS devices having a self-adhesive material applied to the base. The dentist merely removes a Preformed PPS 22 from non-stick sheet 52 and applies it to the dental impression. The body is preferably flexible or pliable so that the Preformed PPS conforms to the contours of the dental impression. Both the adhesive and the body material are water or moisture-resistant so that remaining moisture from the mouth tissues will not interfere with adhesion. The adhesive and the pliable body material are also non-toxic, such as rubber or plastic material. Each Preformed PPS may be provided with its own non-adhesive backing sheet to prevent it from becoming inadvertently adhered before intended. Alternatively, a plurality of Preformed PPS devices may be provided on an enlarged sheet having a non-adhesive or non-stick surface so that individual Preformed PPS devices may be removed and used as needed.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

What is claimed is:

1. A Preformed posterior palatal seal (Preformed PPS) for use in preparation of dentures comprising:
    (a) a body preformed of a predetermined size and a shape of a posterior palatal seal (PPS) for sealing a denture at the "Ah line" of the human palate; and
    (b) means for adhering said preformed body to a denture impression prior to forming a mold from which a denture is to be formed; wherein said means for adhering said body to said impression further comprises:
        i. a flat base formed on said body; and
        ii. a layer of adhesive applied directly to said body which layer of adhesive is composed of a hydrophobic material capable of excluding wetness from a surface of said impression material and adhering to said surface without drying it.

2. A Preformed PPS as in claim 1 further comprising a sheet of removable non-stick material applied to said layer of adhesive to prevent inadvertent sticking prior to removing said non-stick sheet for use of said Preformed PPS on a dental impression.

3. A method of forming a posterior palatal seal on a denture comprising the steps of:

(a) making an impression of a human palate;

(b) identifying on said impression the border between the hard and the soft palate;

(c) adhering a preformed posterior palatal seal having a predetermined shape of a posterior palatal seal to said impression at said identified border;

(d) pouring a dental stone onto said impression with said Preformed PPS adhered thereto to form a model with a PPS channel therein; and (e) molding a denture using said model with said PPS channel therein so that a PPS is integrally formed on said denture.

* * * * *